(12) United States Patent
Sabelle et al.

(10) Patent No.: US 7,422,609 B2
(45) Date of Patent: Sep. 9, 2008

(54) DOUBLE PARA-PHENYLENEDIAMINES JOINED BY AN AROMATIC GROUP FOR DYEING KERATIN FIBERS

(76) Inventors: Stéphane Sabelle, 5, Rue de la Harpe, 75005 Paris (FR); Eric Metais, 44, rue du rû, 95320 St Leu la Forét (FR)

( * ) Notice: Subject to any disclaimer, the term of this patent is extended or adjusted under 35 U.S.C. 154(b) by 167 days.

(21) Appl. No.: 11/476,815

(22) Filed: Jun. 29, 2006

(65) Prior Publication Data

US 2007/0011824 A1    Jan. 18, 2007

Related U.S. Application Data

(60) Provisional application No. 60/698,945, filed on Jul. 14, 2005.

(30) Foreign Application Priority Data

Jun. 29, 2005  (FR) .................................. 05 51806

(51) Int. Cl.
*A61Q 5/10* (2006.01)
*C07C 211/00* (2006.01)

(52) U.S. Cl. .................. 8/405; 8/406; 8/407; 8/408; 8/409; 8/410; 8/411; 8/412; 8/414; 8/415; 8/435; 564/371

(58) Field of Classification Search ............... 8/405, 8/406, 407, 408, 409, 410, 411, 412, 414, 8/415, 435; 564/371
See application file for complete search history.

(56) References Cited

U.S. PATENT DOCUMENTS

| | | | |
|---|---|---|---|
| 2,452,535 A | 10/1948 | Johnson et al. | |
| 3,532,743 A | 10/1970 | Kalopissis et al. | |
| 3,694,138 A | 9/1972 | Kalopissis et al. | |
| 4,003,699 A | 1/1977 | Rose et al. | |
| 4,010,200 A | 3/1977 | Kalopissis et al. | |
| RE30,199 E | 1/1980 | Rose et al. | |
| 4,823,985 A | 4/1989 | Grollier et al. | |
| 5,061,289 A | 10/1991 | Clausen et al. | |
| 5,114,429 A | 5/1992 | Junino et al. | |
| 5,380,340 A | 1/1995 | Neunhoeffer et al. | |
| 5,534,036 A | 7/1996 | Junino et al. | |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,766,576 A | 6/1998 | Lowe et al. | |
| 5,804,171 A | 9/1998 | Audousset et al. | |
| 5,885,564 A | 3/1999 | Zastro et al. | |
| 6,099,592 A | 8/2000 | Vidal et al. | |
| 6,277,156 B1 | 8/2001 | Audousset | |
| 6,284,003 B1 | 9/2001 | Rose et al. | |
| 6,338,741 B1 | 1/2002 | Vidal et al. | |
| 6,379,398 B1 | 4/2002 | Genet et al. | |
| 6,630,004 B1 | 10/2003 | Philippe et al. | |
| 6,645,258 B2 | 11/2003 | Vidal et al. | |
| 6,699,296 B2 | 3/2004 | Chassot | |
| 6,730,789 B1 | 5/2004 | Birault et al. | |
| 6,923,835 B2* | 8/2005 | Sabelle et al. ............... 8/409 |
| 7,303,591 B2* | 12/2007 | Greaves et al. .............. 8/405 |
| 2004/0199018 A1 | 10/2004 | Knuebel et al. | |
| 2006/0265818 A1 | 11/2006 | Seiler et al. | |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| DE | 101 44 226 | 3/2003 |
| EP | 0 714 954 | 6/1996 |
| EP | 0 722 711 | 7/1996 |
| EP | 0 770 375 | 5/1997 |
| EP | 0 872 466 | 10/1998 |
| EP | 0 908 445 | 4/1999 |
| EP | 0 984 006 | 3/2000 |
| EP | 1 396 486 | 3/2004 |
| EP | 1 739 084 | 1/2007 |
| FR | 2 016 123 | 5/1970 |
| FR | 2 586 913 | 3/1987 |
| FR | 2 733 749 | 11/1996 |
| FR | 2 801 308 | 5/2001 |
| GB | 1026978 | 4/1966 |
| GB | 1153196 | 5/1969 |
| JP | 2-019576 | 1/1990 |
| JP | 5-163124 | 6/1993 |
| JP | 8-041329 | 2/1996 |
| WO | WO 94/08969 | 4/1994 |
| WO | WO 94/08970 | 4/1994 |

(Continued)

OTHER PUBLICATIONS

STIC Search Report dated Jan. 24, 2008.*

(Continued)

*Primary Examiner*—Eisa B Elhilo

(57) ABSTRACT

The present disclosure relates to a family of double para-phenylenediamines joined by a linkage comprising an aromatic group and a process for the dyeing of keratin fibers. These double para-phenylenediamines of formula (I) can be used as oxidation base for the dyeing of keratin fibers. Also disclosed are methods of dyeing, methods of making, and dyeing "kits."

24 Claims, No Drawings

FOREIGN PATENT DOCUMENTS

| WO | WO 95/01772 | 1/1995 |
| --- | --- | --- |
| WO | WO 95/15144 | 6/1995 |
| WO | WO 96/15765 | 5/1996 |
| WO | WO 98/01434 | 1/1998 |
| WO | WO 99/11230 | 3/1999 |
| WO | WO 01/72686 | 10/2001 |
| WO | WO 02/06207 | 1/2002 |
| WO | WO 02/055500 | 7/2002 |
| WO | WO 03/024917 | 3/2003 |
| WO | WO 05/051336 | 6/2005 |

OTHER PUBLICATIONS

Co-pending U.S. Appl. No. 11/476,816, Title: Novel Double Para-Phenylenediamines Joined by a Linkage Comprising a Saturated Cyclic Radical and use in Dyeing, Inventors: Stéphane Sabelle et al. U.S. Filing Date: Jun. 29, 2006.
Co-pending U.S. Appl. No. 11/476,823, Title: Novel Double Para-Phenylenediamines Joined by a Branched Aliphatic Group and Method of Dyeing Keratin Fibers, Inventors: Stéphane Sabelle et al. U.S. Filing Date: Jun. 29, 2006.
Co-pending U.S. Appl. No. 11/476,824, Title: Novel Double Para-Phenylenediamines Joined by a Linkage Comprising a Atom Chosen from Sulpher and Nitrogen and Method for Dyeing Keratinous Fibers, Inventors: Stéphane Sabelle et al. U.S. Filing Date: Jun. 29, 2006.
Co-pending U.S. Appl. No. 11/476,822, Title: Novel Double Para-Phenylenediamines Joined by a Linker Arm Substituted with at Least One Group Chosen from Hydroxyl, Alkoxy, and/or Amino Groups and Method of Dyeing Keratinous Fibers, Inventors: Stéphane Sabelle et al. U.S. Filing Date: Jun. 29, 2006.
Co-pending U.S. Appl. No. 11/476,821, Title: Novel Double Para-Phenylenediamines Joined by a Linker Arm Substituted with One or More Carboxylic Radicals and/or Derivatives and use in Dyeing, Inventors: Thierry Bordier et al. U.S. Filing Date: Jun. 29, 2006.
Office Action in co-pending U.S. Appl. No. 11/476,816 dated Mar. 4, 2008, Ex. Eisa Elhilo.
Office Action in co-pending U.S. Appl. No. 11/476,823 dated Mar. 4, 2008, Ex. Eisa Elhilo.
Office Action in co-pending U.S. Appl. No. 11/476,824 dated Mar. 6, 2008, Ex. Eisa Elhilo.
International Search Report for EP 06 11 6056, dated Jul. 10, 2006 (corresponding to U.S. Appl. No. 11/476,816).
International Search Report for EP 06 11 6073, dated Aug. 30, 2006 (corresponding to the present application).
International Search Report for EP 06 11 6072, dated Nov. 13, 2006 (corresponding to U.S. Appl. No. 11/476,823).
International Search Report for EP 06 11 6070, dated Nov. 11, 2006 (corresponding to U.S. Appl. No. 11/476,824).
International Search Report for EP 06 11 6068, dated Nov. 13, 2006 (corresponding to U.S. Appl. No. 11/476,822).
International Search Report for EP 06 11 6066, dated Oct. 31, 2006 (corresponding to U.S. Appl. No. 11/476,821).
International Search Report for FR 0551805, dated Feb. 14, 2006 (corresponding to U.S. Appl. No. 11/476,816).
International Search Report for FR 0551806, dated Feb. 1, 2006 (corresponding to the present application).
International Search Report for FR 0551807, dated May 5, 2006 (corresponding to U.S. Appl. No. 11/476,823).
International Search Report for FR 0551808, dated May 5, 2006 (corresponding to U.S. Appl. No. 11/476,824).
International Search Report for FR 0551809, dated May 5, 2006 (corresponding to U.S. Appl. No. 11/476,822).
International Search Report for FR 0551810, dated May 4, 2006 (corresponding to U.S. Appl. No. 11/476,821).
English Language Derwent Abstract for EP 0 770 375 (1997).
English Language Derwent Abstract for EP 2-019576 (1990).
English Language Derwent Abstract for EP 5-163124 (1993).
English Language Derwent Abstract for EP 8-041329 (1996).
Giastas et al., "Pseudorotaxanes of β-cyclodextrin with diamino end-functionalized oligo-phenyl and -benzyl compounds in solution and in the solid state," *Journal of Inclusion Phenomena and Macrocyclic Chemistry*, 44:247-250 (2002).
Kolsaker et al., "Ozonation of p-nitro-N, N-deimethylaniline," *Advances in Chemistry Series: Ozone Reactions with Organic Compounds*, 112: 101-113 (1972).
Kotsuki et al., "High pressure organic chemistry; XII. A convenient synthesis of aromatic amines from activated aromatic fluorides," *Synthesis*, 12:1147-1148 (1990).
Massa et al., "Spiro-[4-H-pyrrolo[1,-a][1,4]benzodiazepine-4,4'-piperidine]derivatives as potential nootropic agents: a simple one-pot synthesis," *Synth. Comm.*, 20(22):3537-3545 (1990).
Mikuriya et al., "Binuclear nickel(II) complexes of Schiff bases derived from salicylaldehydes and 1,n-diamino-n'-hydroxyalkanes (n,n'=3,2; 4,2; and 5,3) having an endogenous alkoxo bridge and a pyrazolato exogenous bridge," *Bull. Chem. Soc. Jpn.*, 65(2):334-339 (1992).
Mikuriya et al., Alkoxo-bridged dinuclear and tetranuclear copper(II) complexes with Schiff bases derived from benzoylacetone and 1,n-diamino-n'-hydroxyalkanes (n,n'=3,22; 4,2; and 5,3) *Bull. Chem. Soc. Jpn.*, 75:2595-2607 (2002).
Murase et al., "Synthesis and characterization of copper(II) and nikel(H) complexes of 1,5- diamino-3-pentanol and its derivatives," *Bull. Chem. Soc. Jpn.*, 55:2040-2408 (1982).
Nalwa et al., "Aromatic polyureas: a new class of nonlinear optical polymer with large second-harmonic generation," *Electronics Letters*, 28(15): 1409-1411 (1992).
Nir & Seligman, "Ultrastructural localization of oxidase activities in corn root tip cells with two new osmiophillic reagents compared to diaminobenzidine," *Journal of Histochemistry and Cytochemistry*, 19(10): 611-620 (1971).
Pienaar et al., "1-oxo-2,8-diaryl-2,5,8-triaza-1λ-5-phosphabicyclo[3.3.0]octanes as substrates for the preparation of bis(2-arylaminoethyl)amines," *Synthesis*, 9: 1315-1319 (2000).
Seligman et al., "Some cytochemical correlations between oxidase activity (cytochrome and peroxidase) and chemical structure of bis(phenylenediamines)," *Histochemie*, 22: 85-89 (1970).
Sherer et al., "Synthesis and exploratory photophysical investigation of donor-bbridge-acceptor systems derived from N-substituted 4-piperidones," *Recueil des Travaux Chimiques des Pays-Bas*, 112:535-548 (1993).
Winkelmann et al., "Chemotherapeutically active nitro compounds. 1. Nitroanilines," *Arzneimittel-Forschung*, 25(5): 681-708 (1975).
CAS Abstract No. XP001094496; Chen et al., "Chemical behavior of N-aryl nitrogenoxosquaric acid in alcohols,"*Sichuan Daxue Xueba, Ziran Kexue - Acta Acietiarum Naturalium Universitatis Szechuanensis, SSU Ch'Uan Ta Hsueh, Cheng-Tu*, 35(1); 141-143 (1998).
CAS Abstract No. XP002405185 for EP 1 739 084 (2007).

\* cited by examiner

DOUBLE PARA-PHENYLENEDIAMINES JOINED BY AN AROMATIC GROUP FOR DYEING KERATIN FIBERS

CROSS-REFERENCES TO RELATED APPLICATION

This application claims benefit of U.S. Provisional Application No. 60/698,945, filed Jul. 14, 2005, the contents of which are incorporated herein by reference. This application also claims benefit of priority under 35 U.S.C. § 119 to French Patent Application No. FR 05 51806, filed Jun. 29, 2005, the contents of which are also incorporated herein by reference.

FIELD OF THE INVENTION

The present disclosure relates to a novel family of double para-phenylenediamines joined by a linkage comprising an aromatic group and use thereof for the dyeing of keratin fibers.

BACKGROUND OF THE INVENTION

The dyeing of keratin fibers, such as human hair, with dyeing compositions containing oxidation dye precursors, generally called oxidation bases, such as ortho- or para-phenylenediamines, ortho- or para-aminophenols and heterocyclic compounds, is known. These oxidation bases are colorless or weakly colored compounds, which when combined with oxidizing products can give rise, by a process of oxidative condensation, to colored compounds.

It is also known that it is possible to vary the shades obtained with these oxidation bases by combining them with couplers or dyeing modifiers, the latter being chosen, for example, from aromatic meta-diaminobenzenes, meta-aminophenols, meta-diphenols and some heterocyclic compounds, such as indole compounds and pyridine compounds.

The great variety of the molecules employed for the oxidation bases and the couplers means that a rich palette of colors can be obtained.

The so-called "permanent" dyeing obtained using these oxidation dyes should ideally, in addition, satisfy at least one of a number of requirements. Thus, it ideally has no problems of a toxicological nature, makes it possible to obtain the color shades of the desired intensity, has good resistance to external agents such as light, weather, washing, permanent waving, sweat and rubbing, provides coverage of white hair, and/or displays minimum selectivity, i.e., ensures that the smallest possible differences in coloration are obtained all the way along the same keratin fiber, which generally is differently sensitized (i.e., damaged) between its tip and its root.

SUMMARY OF THE INVENTION.

The present disclosure provides novel oxidation bases capable of dyeing keratin fibers in a variety of strong, aesthetic shades with low selectivity, as well as colors that are resistant to the various aggressive factors to which the fibers may be subjected, such as light, sweat and shampoos.

DETAILED DESCRIPTION OF THE INVENTION

The present disclosure thus relates to a cosmetic composition for dyeing keratin fibers, comprising, in a cosmetic medium suitable for dyeing, at least one oxidation base chosen from double para-phenylenediamines of formula (I) and addition salts thereof:

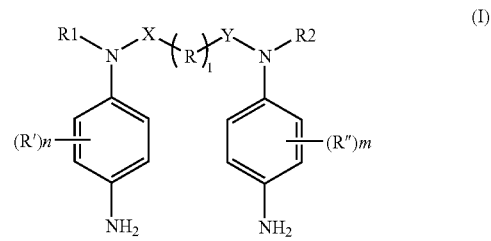

wherein:
R is chosen from aromatic rings with 5 or 6 ring members, optionally containing at least one heteroatom chosen from nitrogen, sulphur and oxygen atoms, it being possible for this ring to be substituted, such as, for example, by at least one radical chosen from $C_1$-$C_4$ alkyl, hydroxyl and hydroxyalkyl radicals, $R_1$ and $R_2$ are chosen from, independently of one another, hydrogen atoms, linear and branched $C_1$-$C_6$ alkyl radicals, which can be substituted by at least one radical chosen from hydroxy, $C_1$-$C_4$ alkoxy, amino, $C_1$-$C_4$ monoalkylamino, and $C_1$-$C_4$ dialkylamino radicals, X and Y are chosen from, independently of one another, linear and branched $C_1$-$C_{10}$ alkylene radicals, R' and R" are chosen from, independently of one another,
$C_1$-$C_6$ alkyl radicals,
$C_1$-$C_6$ alkoxy radicals,
$C_1$-$C_6$ hydroxy-alkoxy radicals,
$C_1$-$C_6$ alkoxy($C_1$-$C_6$)alkyl radicals,
$C_1$-$C_6$ mono- or poly-hydroxy alkyl radicals, n and m are, independently of one another, integers ranging from 0 to 4, and l is an integer equal to 1 or 2.

The present disclosure also relates to a method of dyeing employing this composition, the use of the composition according to the present disclosure for the dyeing of keratin fibers, for example, human keratin fibers such as the hair, and a device with several compartments or dyeing "kit".

The present disclosure also relates to the novel para-phenylenediamines of formula (I) as defined above, with the exception of the para-phenylenediamines of formula:

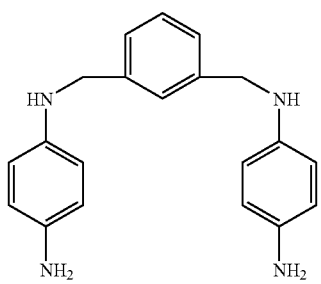

-continued

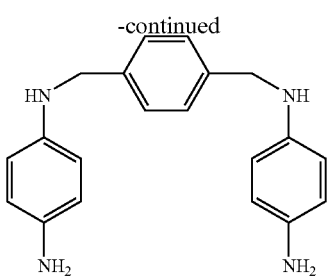

and also the corresponding nitrogen-containing compounds of formula (II) below:

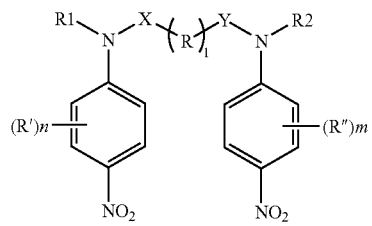

wherein $R_1$, $R_2$, X, Y, R, R', R", n, m and I are as defined above, with the exception of the following nitrogen-containing compounds:

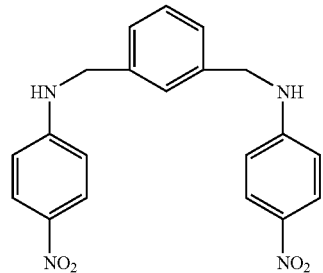

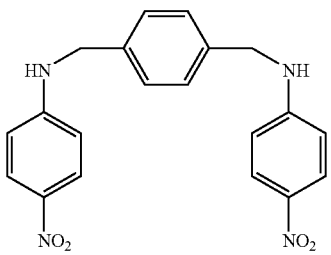

The nitrogen-containing compounds of formula (II) make it possible to obtain, by reduction, para-phenylenediamines of formula (I).

The composition of the present disclosure comprising the para-phenylenediamines of formula (I) makes it possible to obtain very strong dyeing of keratin fibers, of low selectivity, and resistant, for example, to light.

By way of example, the dyeing composition of the present disclosure can comprise, as para-phenylenediamines of formula (I), the following phenylenediamines:

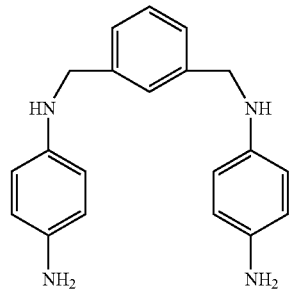

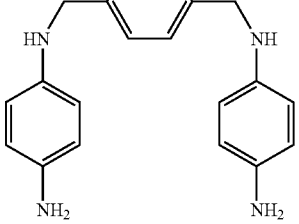

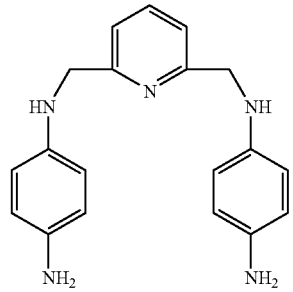

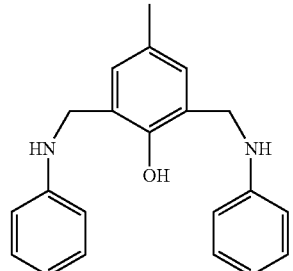

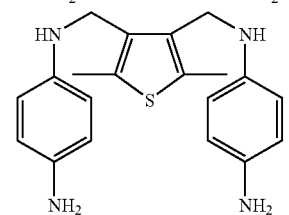

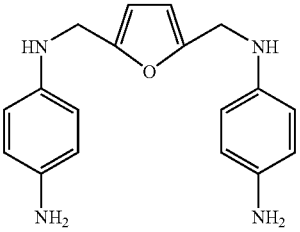

-continued

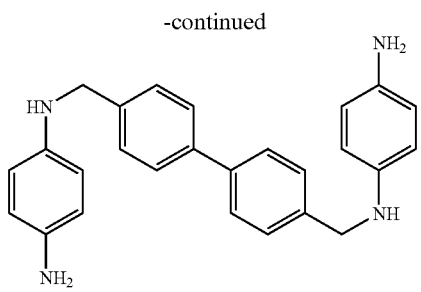

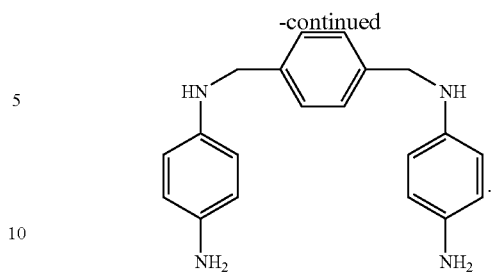

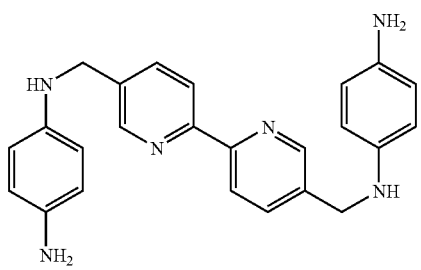

According to at least one embodiment, the composition of the present disclosure comprises para-phenylenediamines of formula (I) such that R is a phenylene radical that can be substituted. $R_1$ and $R_2$ can be chosen independently from hydrogen atoms and $C_1$-$C_4$ alkyl groups that can be substituted, X and Y can be chosen independently from $C_1$-$C_3$ alkylene radicals. n and m can be equal to 0 or 1 and I can be equal to 1.

In at least one embodiment, the addition salts that can be used in the composition of the disclosure may be chosen from salts of addition with an acid, such as hydrochloric acid, hydrobromic acid, sulphuric acid, citric acid, succinic acid, tartaric acid, lactic acid, para-toluene-sulphonic acid, benzene-sulphonic acid, phosphoric acid and acetic acid.

They can also be in the form of solvates, for example a hydrate or a solvate of a linear or branched alcohol such as ethanol or isopropanol.

Among para-phenylenediamines that may be used in the dyeing composition according to at least one embodiment of the present disclosure, non-limiting mention may be made of

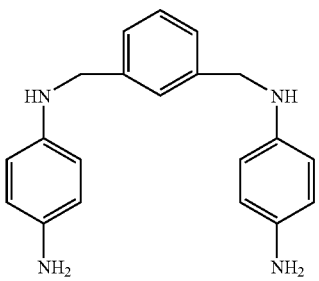

The amount of the at least one para-phenylenediamine of formula (I) in the dyeing composition ranges from 0.0001 wt. % to 20 wt. % relative to the total weight of the composition, such as, for example, from 0.01 wt. % to 10 wt. %.

In at least one embodiment, the composition according to the present disclosure contains at least one oxidation coupler.

Among the oxidation couplers useful herein, non-limiting mention may be made of meta-phenylenediamines, meta-aminophenols, meta-diphenols, naphthalenic couplers, heterocyclic couplers, and addition salts thereof.

As examples of oxidation couplers, non-limiting mention may be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diamino-benzene, 1,3-bis-(2,4-diaminophenoxy)propane, 3-ureido-aniline, 3-ureido-1-dimethylaminobenzene, sesamol, 1-β-hydroxyethylamino-3,4-methylene-dioxybenzene, α-naphthol, 2-methyl-1-naphthol, 6-hydroxy-indole, 4-hydroxy-indole, 4-hydroxy-N-methyl indole, 2-amino-3-hydroxypyridine, 6-hydroxybenzomorpholine, 3,5-diamino-2,6-dimethoxypyridine, 1-N-(β-hydroxyethyl)amino-3,4-methylene dioxybenzene, 2,6-bis-(β-hydroxyethylamino)toluene and addition salts thereof.

The amount of the at least one oxidation coupler can range from 0.0001 wt. % to 20 wt. %, such as, for example, from 0.005 wt. % to 6 wt. % relative to the total weight of the composition.

The composition according to the present disclosure can also contain at least one additional oxidation base different from the oxidation bases of formula (I).

In at least one embodiment, the at least one additional oxidation base can be chosen from para-phenylenediamines, bis-phenylalkylenediamines, para-aminophenols, ortho-aminophenols, heterocyclic bases and addition salts thereof.

Among the para-phenylenediamines that may be used according to the present disclosure, mention may be made of, by way of example: para-phenylenediamine, para-toluenediamine, 2-chloro-para-phenylenediamine, 2,3-dimethyl para-phenylenediamine, 2,6-dimethyl para-phenylenediamine, 2,6-diethyl para-phenylenediamine, 2,5-dimethyl para-phenylenediamine, N,N-dimethyl para-phenylenediamine, N,N-diethyl para-phenylenediamine, N,N-dipropyl para-phenylenediamine, 4-amino-N,N-diethyl-3-methyl aniline, N,N-bis-(β-hydroxyethyl)para-phenylenediamine, 4-N,N-bis-(β-hydroxyethyl)amino-2-methyl aniline, 4-N,N-bis(β-hydroxyethyl)amino-2-chloro-aniline, 2-β-hydroxyethyl para-phenylenediamine, 2-fluoro para-phenylenediamine, 2-isopropyl para-phenylenediamine, N-(β-hydroxypropyl) para-phenylenediamine, 2-hydroxymethyl para-phenylenediamine, N,N-dimethyl-3-methyl para-phenylenediamine, N,N-(ethyl, β-hydroxyethyl)para-phenylenediamine, N-(β,γ-dihydroxypropyl)para-phenylenediamine, N-(4'-aminophenyl)para-phenylenediamine, N-phenyl para-phenylenediamine, 2-β-hydroxyethyloxy para-phenylenediamine, 2-β-acetylaminoethyloxy para-phenylenediamine, N-(β-methoxyethyl)para-phenylenediamine, 4-aminophenylpyrrolidine, 2-thienyl para-phenylenediamine, 2-β-hydroxyethylamino-5-aminotoluene, 3-hydroxy-1-(4'-aminophenyl)pyrrolidone, 6-(4-amino-phenylamino)-hexan-1-ol and acid addition salts thereof.

In at least one further embodiment, the para-phenylenediamines are chosen from para-phenylenediamine, para-toluenediamine, 2-isopropyl para-phenylenediamine, 2-β-hydroxyethyl para-phenylenediamine, 2-β-hydroxyethyloxy para-phenylenediamine, 2,6-dimethyl para-phenylenediamine, 2,6-diethyl para-phenylenediamine, 2,3-dimethyl para-phenylenediamine, N,N-bis-(β-hydroxyethyl)para-phenylenediamine, 2-chloro para-phenylenediamine, 2-β-acetylaminoethyloxy para-phenylenediamine, 6-(4-amino-phenylamino)-hexan-1-ol and acid addition salts thereof.

Among the bis-phenylalkylenediamines, mention may be made of, by way of example: N,N'-bis-(β-hydroxyethyl) N,N'-bis-(4'-aminophenyl) 1,3-diamino-propanol, N,N'-bis (β-hydroxyethyl) N,N'-bis(4'-aminophenyl)ethylenediamine, N,N'-bis-(4'-aminophenyl)tetramethylenediamine, N,N'-bis-(β-hydroxyethyl) N,N'-bis-(4'-aminophenyl)tetramethylenediamine, N,N'-bis-(4'-amino-3'-methylphenyl) tetramethylenediamine, N,N'-bis-(ethyl) N,N'-bis-(4'-amino, 3'-methylphenyl)ethylenediamine, 1,8-bis-(2,5-diamino-phenoxy)-3,6-dioxaoctane, and acid addition salts thereof.

Among the para-aminophenols, mention may be made of, by way of example: para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl aminomethyl)phenol, 4-amino-2-fluorophenol, 4-amino-2,6-dichlorophenol, 4-amino-6[((5'-amino-2'-hydroxy-3'-methyl)phenyl)methyl]-2-methylphenol, bis(5'-amino-2'-hydroxy)phenylmethane and acid addition salts thereof.

Among the ortho-aminophenols, mention may be made of, by way of example: 2-aminophenol, 2-amino-5-methylphenol, 2-amino-6-methylphenol, 5-acetamido-2-aminophenol, 5-[(2-hydroxyethyl)amino]2-methylphenol and acid addition salts thereof.

Among the heterocyclic bases, mention may be made of, by way of example: pyridine derivatives, pyrimidine derivatives and pyrazole derivatives.

Among the pyridine derivatives, mention may be made of the compounds described for example in British Patent Nos. GB 1,026,978 and GB 1,153,196, as well as 2,5-diamino pyridine, 2-(4-methoxyphenyl)amino-3-amino pyridine, 3,4-diamino pyridine, and acid addition salts thereof.

Other pyridine oxidation bases that can be used in the present disclosure are the oxidation bases 3-amino pyrazolo-[1,5-a]-pyridines or their salts of addition described for example in French Patent Application No. FR 2 801 308. By way of example, mention may be made of pyrazolo[1,5-a]pyridin-3-ylamine; 2-acetylamino pyrazolo-[1,5-a]pyridin-3-ylamine; 2-morpholin-4-yl-pyrazolo[1,5-a]pyridin-3-ylamine; 3-amino-pyrazolo[1,5-a]pyridine-2-carboxylic acid; 2-methoxy-pyrazolo[1,5-a]pyridin-3-ylamine; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; 3-amino-pyrazolo[1,5-a]pyridin-7-ol; as well as acid addition salts thereof.

Among the pyrimidine derivatives, mention may be made of the compounds described for example in German Pat No. DE 23 59 399; Japanese Pat Nos. JP 88-169571 and JP 05-63124; European Pat No. EP 0 770 375 or International Pat Application No. WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof and tautomeric forms thereof, when a tautomeric equilibrium exists.

Among the pyrazole derivatives, non-limiting mention may be made of the compounds described in German Pat Nos. DE 38 43 892 and DE 41 33 957, International Pat Application Nos. WO 94/08969 and WO 94/08970, French Patent Application No. FR-A-2 733 749 and German Pat Application No. DE 195 43 988, such as 4,5-diamino-1-methylpyrazole, 4,5-diamino-1-(β-hydroxyethyl)pyrazole, 3,4-diamino pyrazole, 4,5-diamino-1-(4'-chlorobenzyl)pyrazole, 4,5-diamino-1,3-dimethylpyrazole, 4,5-diamino-3-methyl-1-phenyl pyrazole, 4,5-diamino-1-methyl-3-phenyl pyrazole, 4-amino-1,3-dimethyl-5-hydrazino pyrazole, 1-benzyl-4,5-diamino-3-methylpyrazole, 4,5-diamino-3-tert-butyl 1-methylpyrazole, 4,5-diamino-1-tert-butyl 3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl pyrazole, 4,5-diamino-3-methyl-1-isopropyl pyrazole, 4-amino-5-(2'-aminoethyl)amino-1,3-dimethylpyrazole, 3,4,5-triamino pyrazole, 1-methyl-3,4,5-triamino pyrazole, 3,5- diamino-1-methyl-4-methylamino pyrazole, 3,5-diamino-4-(β-hydroxyethyl)amino-1-methylpyrazole, and addition salts thereof.

The additional at least one oxidation base can be present in an amount ranging from 0.0001 wt. % to 20 wt. %, such as, for example, from 0.005 wt. % to 6 wt. % relative to the total weight of the composition.

The dyeing composition according to the present disclosure can additionally contain at least one direct dye which can be chosen from neutral, acid or cationic nitrogen-containing dyes of the benzene series, neutral, acid or cationic direct azo dyes, neutral, acid or cationic quinone direct dyes, including anthraquinone direct dyes, azine direct dyes, methine, azomethine, triarylmethane and indoamine direct dyes and natural direct dyes. In at least one embodiment, the composition according to the present disclosure contains at least one dye chosen from the cationic direct dyes and the natural direct dyes.

Among the cationic direct dyes that can be used according to the present disclosure, non-limiting mention may be made of the cationic azo direct dyes described in International Pat Application Nos. WO 95/15144 and WO-95/01772, and European Patent Application No. EP-0 714 954.

Among these compounds, non-limiting mention may be made of the following dyes:
- 1,3-dimethyl-2-[[4-(dimethylamino)phenyl]azo]-1H-imidazolium chloride,
- 1,3-dimethyl-2-[(4-aminophenyl)azo]-1H-imidazolium chloride, and
- 1-methyl-4-[(methylphenylhydrazono)methyl]-pyridinium methylsulphate.
- Among the natural direct dyes that can be used according to the disclosure, non-limiting mention may be made of lawsone, juglone, alizarin, purpurin, carminic acid, kermesic acid, purpurogallin, protocatechaldehyde, indigo, isatin, curcumine, spinulosine, apigenidine. It is also possible to use extracts or decoctions containing these natural dyes and, for example, henna-based cataplasms or extracts.

In at least one embodiment, the at least one direct dye in present in an amount ranging from 0.001 wt. % to 20 wt. % of the total weight of the ready-to-use composition, such as, for example, from 0.005 wt. % to 10 wt. %.

The cosmetic medium that is suitable for dyeing keratin fibers may comprise water or a mixture of water and at least one organic solvent, for example linear or branched $C_1$-$C_4$ lower alcohols, such as ethanol and isopropanol; the polyols and polyol ethers such as 2-butoxyethanol, propyleneglycol, monomethyl ether of propyleneglycol, monoethyl ether and monomethyl ether of diethyleneglycol, glycerol, as well as the aromatic alcohols such as benzyl alcohol or phenoxyethanol, and mixtures thereof.

In at least one embodiment, the at least one solvent is present in an amount ranging from 1 wt. % to 40 wt. % relative to the total weight of the dyeing composition, such as, for example, from 5 wt. % to 30 wt. %.

In at least one embodiment, the dyeing composition contains at least one cosmetic additive chosen from antioxidants, penetrants, sequestering agents, perfumes, buffers, dispersants, surfactants, conditioners, film-forming agents, polymers, ceramides, preservatives, luster agents, opacifiers, vitamins and provitamins.

The above additives are generally present in an amount, for each of them, ranging from 0.01 wt. % to 20 wt. % relative to the weight of the composition.

The pH of the composition according to the disclosure can range from 3 to 12, such as, for example, from 5 to 11. It can be adjusted to the desired value by acidifying or alkalizing agents usually employed in the dyeing of keratin fibers or alternatively by conventional buffering systems.

Among the acidifying agents, mention may be made of, by way of example, inorganic or organic acids other than the dicarboxylic acids such as hydrochloric acid, orthophosphoric acid, sulphuric acid, carboxylic acids such as acetic acid, tartaric acid, citric acid, lactic acid, and sulphonic acids.

Among the alkalizing agents, mention may be made of, by way of example: ammonia, alkali metal carbonates, alkanolamines such as the mono-, di- and triethanolamines as well as their derivatives, the hydroxides of sodium or of potassium and the compounds of formula:

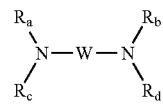

wherein W is a propylene residue optionally substituted by a hydroxyl group or a $C_1$-$C_4$ alkyl radical; $R_a$, $R_b$, $R_c$ and $R_d$, which may be identical or different, are chosen from hydrogen atoms, $C_1$-$C_4$ alkyl radicals and $C_1$-$C_4$ hydroxyalkyl radicals.

Of course, a person skilled in the art will ensure that the additive or additives, precursors of additional oxidation dyes, oxidation couplers and direct dyes are selected in such a way that the advantageous properties intrinsically associated with the oxidation dyeing composition according to the present disclosure are not, or substantially are not, adversely affected by the envisaged addition(s).

The dyeing composition according to the present disclosure can be in various forms, such as in the form of liquids, creams, gels, or in any other form that is suitable for carrying out dyeing of keratin fibers, including human hair.

The present disclosure further relates to a method of dyeing of keratin fibers in which the composition of the disclosure as defined previously is applied to the keratin fibers, and the color is developed by an oxidizing agent. The color can be developed at acid, neutral or alkaline pH. The oxidizing agent can be added to the composition of the disclosure right at the moment of use. It can be applied using an oxidizing composition containing it, applied simultaneously or sequentially with the composition of the disclosure.

As oxidizing agents, non-limiting mention may be made of hydrogen peroxide, urea peroxide, bromates of alkali metals, per-salts such as perborates and persulphates, peracids and oxidase enzymes among which mention may be made of the peroxidases, 2-electron oxido-reductases such as the uricases and 4-electron oxygenases such as the laccases. In at least one embodiment, hydrogen peroxide is used.

According to at least one embodiment, the composition according to the present disclosure is mixed, for example at the moment of use, with a composition containing, in a medium that is suitable for dyeing, at least one oxidizing agent, this oxidizing agent being present in a sufficient amount for dye development. The mixture obtained is then applied to the keratin fibers. After a holding time of about 3 to 50 minutes, such as from 5 to 30 minutes, the keratin fibers are rinsed, washed with shampoo, rinsed again and then dried.

The oxidizing composition can contain various additives used conventionally in compositions for hair dyeing and as defined previously.

The pH of the oxidizing composition containing the oxidizing agent may be such that after mixing with the dyeing composition, the pH of the resulting composition applied to the keratin fibers may range from 3 to 12, such as, for example, from 5 and 11. It can be adjusted to the desired value by acidifying or alkalizing agents usually employed for dyeing of keratin fibers and as defined previously.

The ready-to-use composition that is finally applied to the keratin fibers can be in various forms, such as in the form of liquids, creams, gels or in any other form that is suitable for carrying out dyeing of keratin fibers, including human keratin fibers, such as human hair.

The present disclosure also relates to the use of the composition according to the present disclosure containing, in a medium that is suitable for dyeing, at least one para-phenylenediamine of formula (I) for the dyeing of keratin fibers, including human keratin fibers such as the hair.

The present disclosure also relates to a multi-compartment device or dyeing "kit" in which a first compartment contains a composition comprising at least one oxidation base of formula (I) as defined above and a second compartment contains an oxidizing composition. This kit can be equipped with an applicator for delivering the desired mixture onto the hair, such as the kits described in French Patent No. FR-2 586 913.

The para-phenylenediamines of formula (I) according to the present disclosure can be prepared according to a conventional method of synthesis. Reference may be made for example to German Patent Application No. DE 101 44 226 A.

By way of illustration, the para-phenylenediamines of formula (I) can be synthesized according to the following reaction scheme:

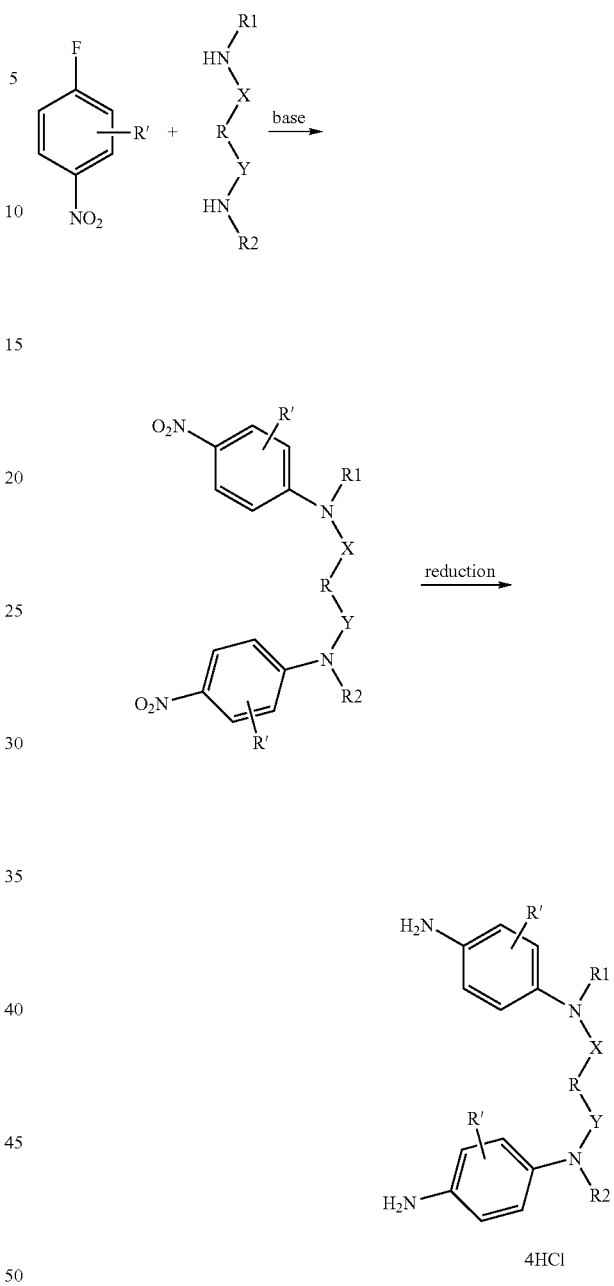

The first stage in the synthesis is a nucleophilic substitution of a diamine on a derivative of para-fluoro-nitrobenzene, a stage suggested by the publications Synthesis 1990 (12), 1147-1148 and Synth. Commun. 1990, 20 (22), 3537-3545. The second stage is a conventional reduction stage, and can be for example a reaction of hydrogenation by heterogeneous catalysis in the presence of Pd/C, Pd(II)/C, Raney Nickel or a reaction of reduction by a metal, for example by zinc, iron, tin, etc. (Advanced Organic Chemistry, 4th edition, 1992, J. March, Wiley Interscience; Reduction in Organic Chemistry, M. Hudlicky, 1983, Ellis Horwood Series Chemical Science).

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow serve to illustrate the present disclosure without, however, being limiting in nature.

EXAMPLES OF SYNTHESIS

Example 1

Synthesis of N-(3-{[(4-aminophenyl)amino]methyl}benzyl)benzene-1,4-diamine tetrahydrochloride (2)

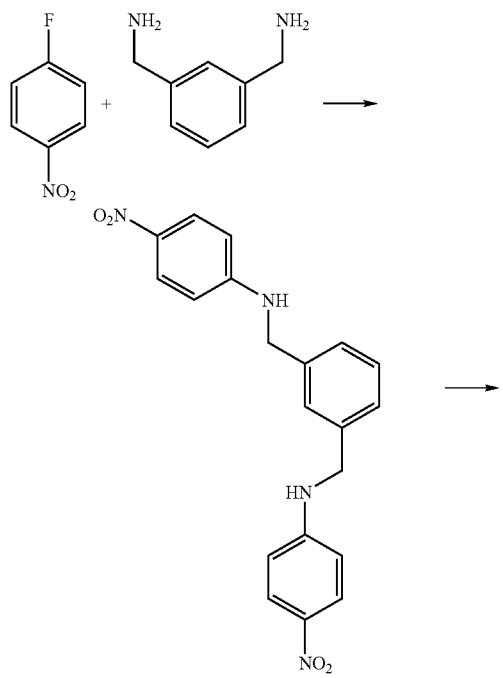

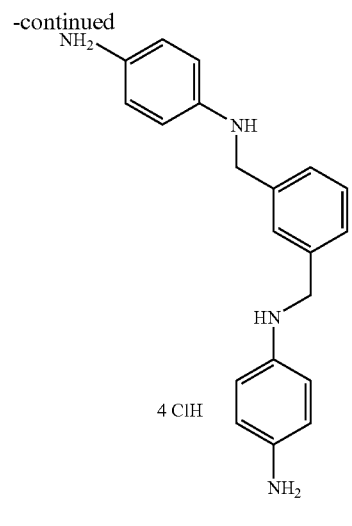

Stage 1: synthesis of 4-nitro-N-(3-{[(4-nitrophenyl)amino]methyl}benzyl)aniline (1)

1.73 g of para-fluoronitrobenzene (2 eq.) were dissolved in 5 ml of DMSO. 1.2 equivalents of m-xylenediamine and 4 equivalents of triethylamine were added to the solution. The reaction mixture was heated at 60° C. for 20 hours. The mixture was then poured onto crushed ice and a precipitate formed. The latter was filtered, washed with water, and then dried.

Stage 2: synthesis of N-(3-{[(4-aminophenyl)amino]methyl}benzyl)benzene-1,4-diamine tetrahydrochloride (2)

The mixture of powdered zinc (30 g), ammonium chloride (3 g), water (5 ml) and absolute ethanol were brought to reflux with the oil bath. The 4-nitro-N-(3-{[(4-nitrophenyl)amino]methyl}benzyl)aniline (3 g) was dissolved in 50 ml of NMP and introduced dropwise until there was decoloration of the reaction medium, while at the same time the reflux was maintained.

The mixture was filtered over celite, under hot conditions, and the filtrate was recovered in a mixture of ethanol and concentrated hydrochloric acid. After the addition of isopropanol, the mixture was concentrated under vacuum until there was precipitation of a solid corresponding to the N-(3-{[(4-aminophenyl)amino]methyl}benzyl)benzene-1,4-diamine tetrahydrochloride (2).

The proton and mass NMR spectra corresponded to the expected structure of the product.

Example 2

Synthesis of N-(4-{[(4-aminophenyl)amino]methyl}benzyl)benzene-1,4-diamine tetrahydrochloride (4)

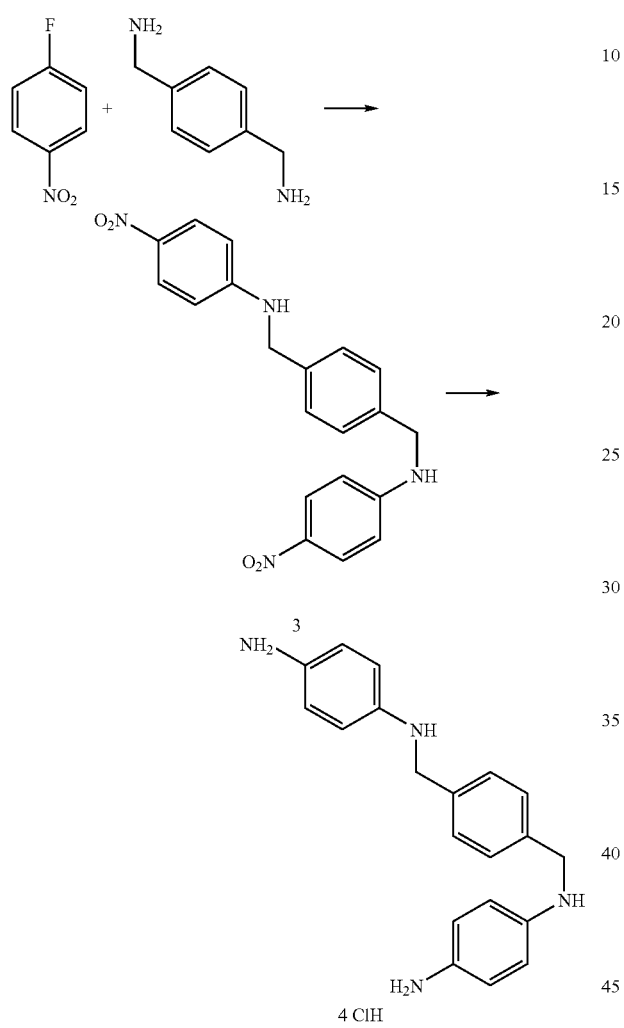

Stage 1: synthesis of 4-nitro-N-(4-{[(4-nitrophenyl)amino]methyl}benzyl)aniline (3)

4 g of para-fluoronitrobenzene (2 eq.) was dissolved in 5 ml of DMSO. 1.2 equivalents of α,α-diamino-p-xylene and 4 equivalents of triethylamine were added to the solution. The reaction mixture was heated at 60° C. for 24 hours. The mixture was then poured onto crushed ice and a precipitate formed. The latter was filtered, washed with water, and then dried.

Stage 2: synthesis of N-(4-{[(4-aminophenyl)amino]methyl}benzyl)benzene-1,4-diamine tetrahydrochloride (4)

The mixture of powdered zinc (22.2 g), ammonium chloride (2.5 g), water (4 ml) and absolute ethanol (20 ml) were brought to reflux with the oil bath. The 4-nitro-N-(4-{[(4-nitrophenyl)amino]methyl}benzyl)aniline (3.4 g) was dissolved in 20 ml of NMP and introduced dropwise until there was decoloration of the reaction medium, while at the same time the reflux was maintained.

The mixture was filtered over celite, under hot conditions, and the filtrate was recovered in a mixture of ethanol and concentrated hydrochloric acid. After the addition of isopropanol, the mixture was concentrated under vacuum so as to obtain a solid corresponding to the N-(4-{[(4-aminophenyl)amino]methyl}benzyl)benzene-1,4-diamine tetrahydrochloride (4).

The proton and mass NMR spectra corresponded to the expected structure of the product.

EXAMPLES OF DYEING

Examples 1 to 14

Dyeing Composition Based on N-(4-{[(4-aminophenyl)amino]methyl}benzyl)benzene-1,4-diamine tetrahydrochloride (4)

Examples 1 to 7

Dyeing in an Acid Medium

The following dyeing compositions were prepared:

|  | Example | | | | | | |
| --- | --- | --- | --- | --- | --- | --- | --- |
|  | 1 | 2 | 3 | 4 | 5 | 6 | 7 |
| N-(4-{[(4-Aminophenyl)amino]methyl}benzyl)benzene-1,4-diamine tetrahydrochloride (4) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methyl-phenol | | $10^{-3}$ mol | | | | | |
| 1H-Indol-6-ol | | | $10^{-3}$ mol | | | | |
| 2-Amino-pyridin-3-ol | | | | $10^{-3}$ mol | | | |
| 3.6-Dimethyl-1H-pyrazolo[5,1-c][1,2,4]triazole | | | | | $10^{-3}$ | | |

-continued

|  | Example | | | | | | |
|---|---|---|---|---|---|---|---|
|  | 1 | 2 | 3 | 4 | 5 | 6 | 7 |
|  |  |  |  | mol |  |  |  |
| 2-(2,4-diamino-phenoxy)-ethanol hydrochloride |  |  |  |  |  | $10^{-3}$ mol |  |
| 3-Amino-2-chloro-6-methyl-phenol hydrochloride |  |  |  |  |  |  | $10^{-3}$ mol |
| Dyeing support (1) | (*) | (*) | (*) | (*) | (*) | (*) | (*) |
| Demineralized water q.s.f. | 100 g | 100 g | 100 g | 100 g | 100 g | 100 g | 100 g |

(*): dyeing support (1) pH 7

| 96° ethanol | 20.8 g |
|---|---|
| Sodium metabisulphite, 35% aqueous solution | 0.23 g M.A |
| Pentasodium salt of diethylene-triamine-pentaacetic acid, 40% aqueous solution | 0.48 g M.A |
| $C_8$-$C_{10}$ alkyl polyglycoside, 60% aqueous solution | 3.6 g M.A |
| Benzyl alcohol | 2.0 g |
| Polyethylene glycol with 8 ethylene oxide units | 3.0 g |
| $Na_2HPO_4$ | 0.28 g |
| $KH_2PO_4$ | 0.46 g |

At the moment of use, each composition was mixed with an equal weight of hydrogen peroxide at 20 volumes (6 wt. %). A final pH of 7 was obtained.

|  | Example | | | | | | |
|---|---|---|---|---|---|---|---|
|  | 1 | 2 | 3 | 4 | 5 | 6 | 7 |
| Shade observed | yellow | deep red | deep red-brown | deep red-brown | orangey | deep blue | deep grey violet-red |

Examples 8 to 14

Dyeing in a Basic Medium

The following dyeing compositions were prepared:

|  | Example | | | | | | |
|---|---|---|---|---|---|---|---|
|  | 8 | 9 | 10 | 11 | 12 | 13 | 14 |
| N-(4-{[(4-Aminophenyl)-amino]methyl}benzyl)-benzene-1,4-diamine tetrahydrochloride (4) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol |  |  |  |  |  |  |
| 5-Amino-2-methyl-phenol |  | $10^{-3}$ mol |  |  |  |  |  |
| 1H-Indol-6-ol |  |  | $10^{-3}$ mol |  |  |  |  |
| 2-Amino-pyridin-3-ol |  |  |  | $10^{-3}$ mol |  |  |  |
| 3.6-Dimethyl-1H-pyrazolo[5,1-c][1,2,4]triazole |  |  |  |  | $10^{-3}$ mol |  |  |
| 2-(2,4-Diamino-phenoxy)-ethanol hydrochloride |  |  |  |  |  | $10^{-3}$ mol |  |
| 3-Amino-2-chloro-6-methyl-phenol hydrochloride |  |  |  |  |  |  | $10^{-3}$ mol |
| Dyeing support (2) | (*) | (*) | (*) | (*) | (*) | (*) | (*) |
| Demineralized water q.s.f. | 100 g | 100 g | 100 g | 100 g | 100 g | 100 g | 100 g |

(*): dyeing support (2) pH 9.5

Each mixture obtained was applied to locks of grey hair at 90% white. After a holding time of 30 minutes, the locks were rinsed, washed with a standard shampoo, rinsed again and then dried. The shades obtained are shown in the following table:

| 96° ethanol | 20.8 g |
|---|---|
| Sodium metabisulphite, 35% aqueous solution | 0.23 g M.A |

-continued

| | |
|---|---|
| Pentasodium salt of diethylene-triamine-pentaacetic acid, 40% aqueous solution | 0.48 g MA |
| C$_8$-C$_{10}$ alkyl polyglycoside, 60% aqueous solution | 3.6 g M.A |
| Benzyl alcohol | 2.0 g |
| Polyethylene glycol with 8 ethylene oxide units | 3.0 g |
| NH$_4$Cl | 4.32 g |
| Ammonia at 20% NH$_3$ | 2.94 g |

At the moment of use, each composition was mixed with an equal weight of hydrogen peroxide at 20 volumes (6 wt. %). A final pH of 9.5 was obtained.

Each mixture obtained was applied to locks of grey hair at 90% white. After a holding time of 30 minutes, the locks were rinsed, washed with a standard shampoo, rinsed again and then dried.

The shades obtained are shown in the following table:

| | Example | | | | | | |
|---|---|---|---|---|---|---|---|
| | 8 | 9 | 10 | 11 | 12 | 13 | 14 |
| Shade observed | yellow | deep red-brown | deep red-brown | deep red-brown | or-angey | deep grey-blue | deep grey violet-red |

What is claimed is:

1. A cosmetic composition for dyeing keratin fibers, comprising, in a suitable cosmetic medium, at least one oxidation base chosen from para-phenylenediamines of formula (I) and addition salts thereof:

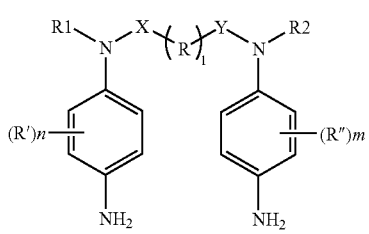

wherein:
R is an aromatic ring with 5 or 6 ring members, optionally comprising at least one heteroatom chosen from nitrogen, sulphur and oxygen atoms; wherein the aromatic ring is optionally substituted;
R$_1$ and R$_2$ are chosen from, independently of one another, hydrogen atoms; and
linear and branched C$_1$-C$_6$ alkyl radicals optionally substituted by at least one radical chosen from hydroxy, C$_1$-C$_4$ alkoxy, amino, C$_1$-C$_4$ monoalkylamino, and C$_1$-C$_4$ dialkylamino radicals;
X and Y are chosen from, independently of one another, linear and branched C$_1$-C$_{10}$ alkylene radicals;
R' and R" are chosen from, independently of one another, C$_1$-C$_6$ alkyl radicals;
C$_1$-C$_6$ alkoxy radicals;
C$_1$-C$_6$ hydroxy-alkoxy radicals;
C$_1$-C$_6$ alkoxy(C$_1$-C$_6$)alkyl radicals; and
C$_1$-C$_6$ mono- and poly-hydroxy alkyl radicals;
n and m are, independently of one another, integers ranging from 0 to 4; and
l is an integer equal to 1 or 2.

2. The composition according to claim 1, wherein R is a phenylene radical that is optionally substituted.

3. The composition according to claim 1, wherein R$_1$ and R$_2$ are chosen from, independently of one another, hydrogen atoms and C$_1$-C$_4$ alkyl groups which are optionally substituted.

4. The composition according to claim 1, wherein X and Y are chosen from, independently of one another, C$_1$-C$_3$ alkylene radicals.

5. The composition according to claim 1, wherein R is optionally substituted with at least one radical chosen from C$_1$-C$_4$ alkyl, hydroxyl and hydroxyalkyl radicals.

6. The composition according to claim 1, wherein the para-phenylenediamines of formula (I) are chosen from:

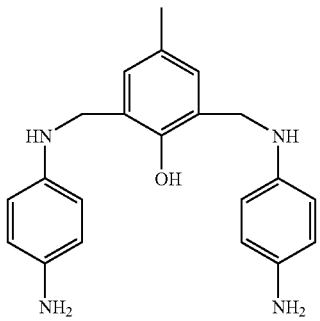

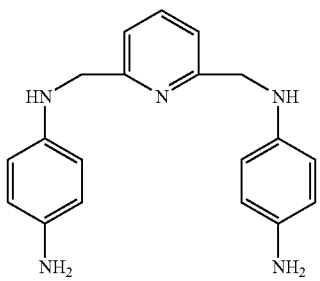

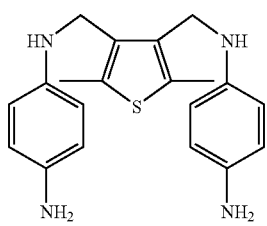

-continued

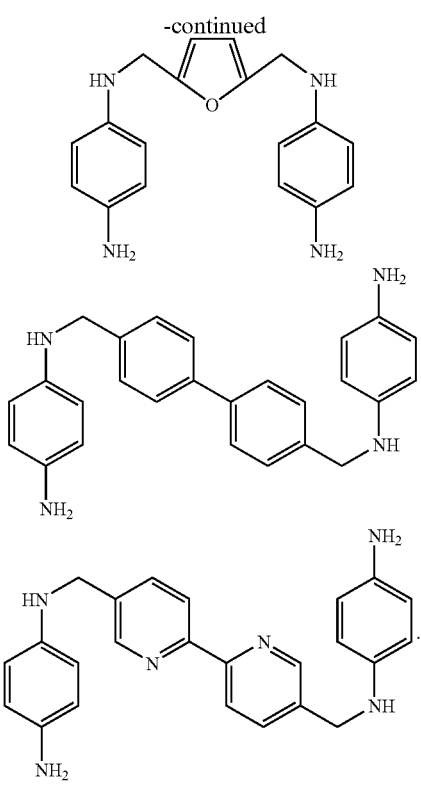

7. The composition according to claim 1, wherein the addition salts are chosen from addition salts of acids chosen from hydrochloric acid, hydrobromic acid, sulphuric acid, citric acid, succinic acid, tartaric acid, lactic acid, para-toluenesulphonic acid, benzene-sulphonic acid, phosphoric acid and acetic acid, wherein said salts are optionally in the form of solvates.

8. The composition according to claim 1, wherein the at least one oxidation base is present in an amount ranging from 0.0001 wt. % to 20 wt. % relative to the total weight of the composition.

9. The composition according to claim 8, wherein the at least one oxidation base is present in an amount ranging from 0.01 wt. % to 10 wt. % relative to the total weight of the composition.

10. The composition according to claim 1, further comprising at least one oxidation coupler.

11. The composition according to claim 10, wherein the at least one oxidation coupler is chosen from meta-phenylenediamines, meta-aminophenols, meta-diphenols, naphthalenic couplers, heterocyclic couplers, and addition salts thereof.

12. The composition according to claim 1, further comprising at least one additional oxidation base different from the para-phenylenediamines of formula (I).

13. The composition according to claim 12, wherein the at least one additional oxidation base is chosen from para-phenylenediamines, bis-phenylalkylenediamines, para-aminophenols, ortho-aminophenols, heterocyclic bases, and addition salts thereof.

14. The composition according to claim 1, further comprising at least one direct dye.

15. The composition according to claim 1, wherein the suitable cosmetic medium comprises water optionally comprising at least one organic solvent.

16. The composition according to claim 15, wherein the at least one organic solvent is chosen from linear and branched $C_1$-$C_4$ lower alcohols, aromatic alcohols, and mixtures thereof.

17. The composition according to claim 1, further comprising at least one cosmetic additive chosen from antioxidants, penetrants, sequestering agents, perfumes, buffers, dispersants, surfactants, conditioners, film-forming agents, polymers, ceramides, preservatives, luster agents, opacifiers, vitamins and provitamins.

18. The composition according to claim 17, wherein the at least one cosmetic additive is present in an amount, for each cosmetic additive, ranging from 0.01 wt. % to 20 wt. % relative to the total weight of the composition.

19. The composition according to claim 1, further comprising an oxidizing agent.

20. A method for dyeing of keratin fibers, comprising applying to said fibers at least one dyeing composition, in the presence of an oxidizing agent, for a sufficient time for development of a desired coloration, wherein the at least one dyeing composition comprises, in a suitable cosmetic medium, at least one oxidation base chosen from para-phenylenediamines of formula (I) and addition salts thereof:

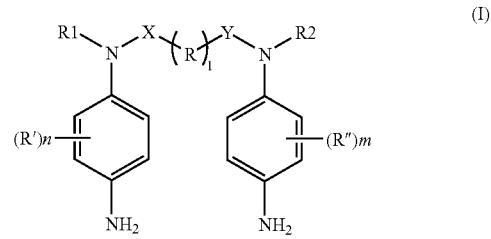

(I)

wherein:
R is an aromatic ring with 5 or 6 ring members, optionally comprising at least one heteroatom chosen from nitrogen, sulphur and oxygen atoms; wherein the aromatic ring is optionally substituted;

$R_1$ and $R_2$ are chosen from, independently of one another, hydrogen atoms; and linear and branched $C_1$-$C_6$ alkyl radicals optionally substituted by at least one radical chosen from hydroxy, $C_1$-$C_4$ alkoxy, amino, $C_1$-$C_4$ monoalkylamino, and $C_1$-$C_4$ dialkylamino radicals;

X and Y are chosen from, independently of one another, linear and branched $C_1$-$C_{10}$ alkylene radicals;

R' and R" are chosen from, independently of one another,
$C_1$-$C_6$ alkyl radicals;
$C_1$-$C_6$ alkoxy radicals;
$C_1$-$C_6$ hydroxy-alkoxy radicals;
$C_1$-$C_6$ alkoxy($C_1$-$C_6$)alkyl radicals; and
$C_1$-$C_6$ mono- and poly-hydroxy alkyl radicals;

n and m are, independently of one another, integers ranging from 0 to 4; and l is an integer equal to 1 or 2.

21. A multi-compartment kit, comprising a first compartment comprising a composition for dyeing keratin fibers and a second compartment comprising an oxidizing agent, wherein the composition for dyeing keratin fibers comprises, in a suitable cosmetic medium, at least one oxidation base chosen from para-phenylenediamines of formula (I) and addition salts thereof:

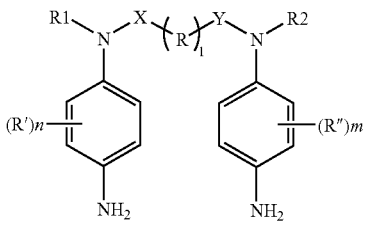

wherein:
- R is an aromatic ring with 5 or 6 ring members, optionally comprising at least one heteroatom chosen from nitrogen, sulphur and oxygen atoms; wherein the aromatic ring is optionally substituted;
- $R_1$ and $R_2$ are chosen from, independently of one another, hydrogen atoms; and
  linear and branched $C_1$-$C_6$ alkyl radicals optionally substituted by at least one radical chosen from hydroxy, $C_1$-$C_4$ alkoxy, amino, $C_1$-$C_4$ monoalkylamino, and $C_1$-$C_4$ dialkylamino radicals;
- X and Y are chosen from, independently of one another, linear and branched $C_1$-$C_{10}$ alkylene radicals;
- R' and R" are chosen from, independently of one another,
  $C_1$-$C_6$ alkyl radicals;
  $C_1$-$C_6$ alkoxy radicals;
  $C_1$-$C_6$ hydroxy-alkoxy radicals;
  $C_1$-$C_6$ alkoxy($C_1$-$C_6$)alkyl radicals; and
  $C_1$-$C_6$ mono- and poly-hydroxy alkyl radicals;
- n and m are, independently of one another, integers ranging from 0 to 4; and
- l is an integer equal to 1 or 2.

22. A para-phenylenediamine compound chosen from compounds of formula (I) and addition salts thereof:

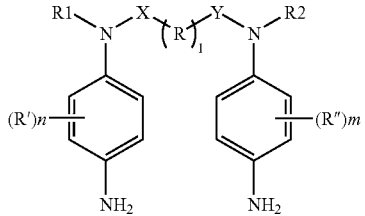

wherein:
- R is an aromatic ring with 5 or 6 ring members, optionally comprising at least one heteroatom chosen from nitrogen, sulphur and oxygen atoms; wherein the aromatic ring is optionally substituted;
- $R_1$ and $R_2$ are chosen from, independently of one another, hydrogen atoms; and
  linear and branched $C_1$-$C_6$ alkyl radicals optionally substituted by at least one radical chosen from hydroxy, $C_1$-$C_4$ alkoxy, amino, $C_1$-$C_4$ monoalkylamino, and $C_1$-$C_4$ dialkylamino radicals;
- X and Y are chosen from, independently of one another, linear and branched $C_1$-$C_{10}$ alkylene radicals;
- R' and R" are chosen from, independently of one another,
  $C_1$-$C_6$ alkyl radicals;
  $C_1$-$C_6$ alkoxy radicals;
  $C_1$-$C_6$ hydroxy-alkoxy radicals;
  $C_1$-$C_6$ alkoxy($C_1$-$C_6$)alkyl radicals; and
  $C_1$-$C_6$ mono- and poly-hydroxy alkyl radicals;
- n and m are, independently of one another, integers ranging from 0 to 4; and
- l is an integer equal to 1 or 2;
with the exception of the compounds

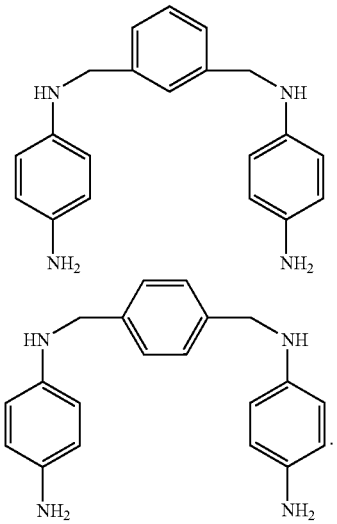

23. A nitrogen-containing compound of formula (II)

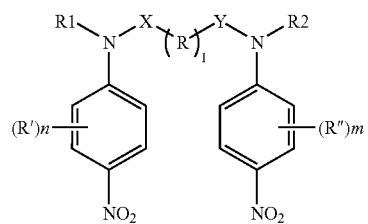

wherein:
- R is an aromatic ring with 5 or 6 ring members, optionally comprising at least one heteroatom chosen from nitrogen, sulphur and oxygen atoms; wherein the aromatic ring is optionally substituted;
- $R_1$ and $R_2$ are chosen from, independently of one another, hydrogen atoms; and
  linear and branched $C_1$-$C_6$ alkyl radicals optionally substituted by at least one radical chosen from hydroxy, $C_1$-$C_4$ alkoxy, amino, $C_1$-$C_4$ monoalkylamino, and $C_1$-$C_4$ dialkylamino radicals;
- X and Y are chosen from, independently of one another, linear and branched $C_1$-$C_{10}$ alkylene radicals;
- R' and R" are chosen from, independently of one another,
  $C_1$-$C_6$ alkyl radicals;
  $C_1$-$C_6$ alkoxy radicals;
  $C_1$-$C_6$ hydroxy-alkoxy radicals;
  $C_1$-$C_6$ alkoxy($C_1$-$C_6$)alkyl radicals; and
  $C_1$-$C_6$ mono- and poly-hydroxy alkyl radicals;
- n and m are, independently of one another, integers ranging from 0 to 4; and
- l is an integer equal to 1 or 2;
with the exception of the compounds

24. A method of preparing a para-phenylenediamine of formula (I),

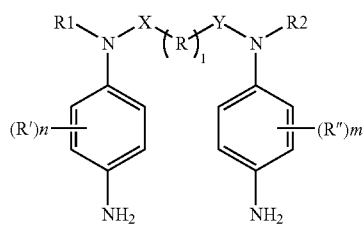

with the exception of the compounds

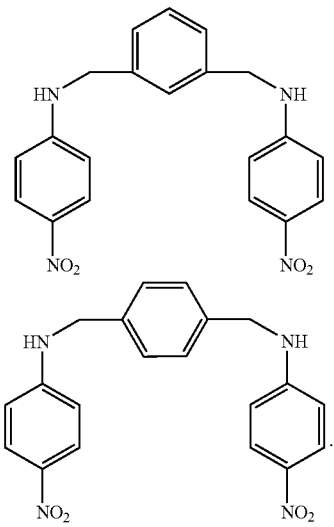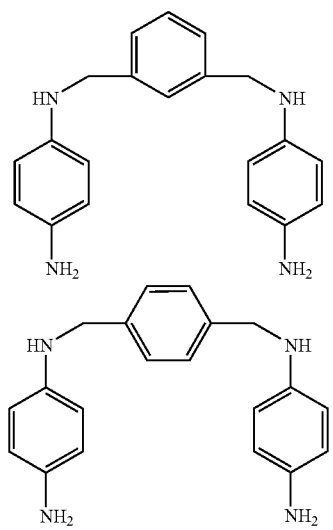

comprising reducing a compound of formula (II),

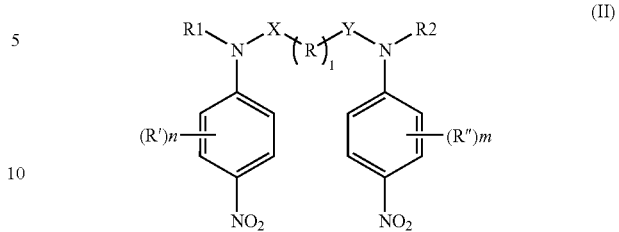

with the exception of the compounds

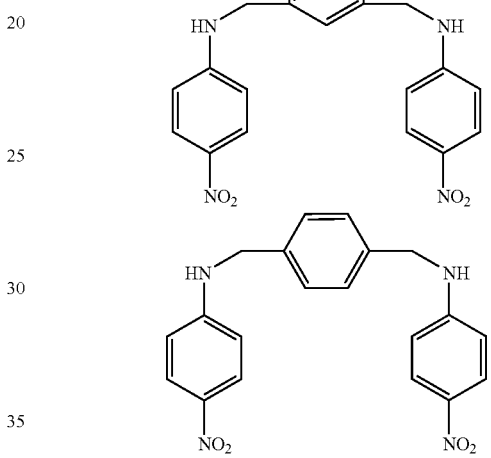

wherein:
R is an aromatic ring with 5 or 6 ring members, optionally comprising at least one heteroatom chosen from nitrogen, sulphur and oxygen atoms; wherein the aromatic ring is optionally substituted;
$R_1$ and $R_2$ are chosen from, independently of one another, hydrogen atoms; and
linear and branched $C_1$-$C_6$ alkyl radicals optionally substituted by at least one radical chosen from hydroxy, $C_1$-$C_4$ alkoxy, amino, $C_1$-$C_4$ monoalkylamino, and $C_1$-$C_4$ dialkylamino radicals;
X and Y are chosen from, independently of one another, linear and branched $C_1$-$C_{10}$ alkylene radicals;
R' and R" are chosen from, independently of one another, $C_1$-$C_6$ alkyl radicals;
$C_1$-$C_6$ alkoxy radicals;
$C_1$-$C_6$ hydroxy-alkoxy radicals;
$C_1$-$C_6$ alkoxy($C_1$-$C_6$)alkyl radicals; and
$C_1$-$C_6$ mono- and poly-hydroxy alkyl radicals;
n and m are, independently of one another, integers ranging from 0 to 4; and
l is an integer equal to 1 or 2.

* * * * *

UNITED STATES PATENT AND TRADEMARK OFFICE
CERTIFICATE OF CORRECTION

PATENT NO. : 7,422,609 B2
APPLICATION NO. : 11/476815
DATED : September 9, 2008
INVENTOR(S) : Stéphane Sabelle et al.

It is certified that error appears in the above-identified patent and that said Letters Patent is hereby corrected as shown below:

In claim 1, column 20, line 7, "I is" should read --1 is--.

In claim 20, column 22, line 60, "I is" should read --1 is--.

In claim 21, column 23, line 34, "I is" should read --1 is--.

In claim 22, column 24, line 4, "I is" should read --1 is--.

In claim 23, column 24, line 66, "I is" should read --1 is--.

In claim 24, column 26, line 60, "I is" should read --1 is--.

Signed and Sealed this

Seventh Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,422,609 B2
APPLICATION NO. : 11/476815
DATED : September 9, 2008
INVENTOR(S) : Stéphane Sabelle et al.

It is certified that error appears in the above-identified patent and that said Letters Patent is hereby corrected as shown below:

On the title page, insert --(73)   Assignee: L'Oréal S.A., Paris (FR)--.

On the title page, insert --(74)   Attorney, Agent, or Firm—Finnegan, Henderson, Farabow, Garrett & Dunner, L.L.P.--.

Signed and Sealed this

Twenty-fourth Day of November, 2009

David J. Kappos
*Director of the United States Patent and Trademark Office*